United States Patent [19]

Kuch et al.

[11] 4,391,756

[45] Jul. 5, 1983

[54] ORGANO-MONOVALENT AURUS COMPLEX CATALYSTS FOR THE MANUFACTURE OF OLEFIN OXIDES

[75] Inventors: Philip L. Kuch, Warrensville Heights; Daniel R. Herrington, Chesterland; Janet M. Eggett, Parma, all of Ohio

[73] Assignee: The Standard Oil Company, Cleveland, Ohio

[21] Appl. No.: 969,124

[22] Filed: Dec. 13, 1978

Related U.S. Application Data

[62] Division of Ser. No. 912,620, Jun. 5, 1978, abandoned.

[51] Int. Cl.³ .............................. C07F 1/12; B01J 31/24; B01J 31/18; B01J 31/26
[52] U.S. Cl. .................................. 260/430; 252/429 R; 252/430; 252/431 R; 252/431 P; 549/533
[58] Field of Search .......... 252/431 R, 431 P, 431 N, 252/429 R; 260/430, 348.33; 568/867; 549/533

[56] References Cited

U.S. PATENT DOCUMENTS 3,635,945 1/1972 Nemeth et al. ..................... 260/430

FOREIGN PATENT DOCUMENTS 46-9691 3/1971 Japan .............................. 260/348.33

OTHER PUBLICATIONS

Journal of the Chemical Society–(London)–1937, "The Constitution of Complex Metallic Salts," F. G. Mann et al.–pp. 1828–1836.
Journal Inorg. Nucl. Chem.–1968–vol. 30, p. 1328, "Bis(triphenylphosphine)Gold (I) Halides".
Journal Organometal. Chem. 26, (1971), pp. 417–430, "Homogenous Catalysis . . . ," A. Fusi et al.

Primary Examiner—P. E. Konopka
Attorney, Agent, or Firm—Gary R. Plotecher; Herbert D. Knudsen; Larry W. Evans

[57] ABSTRACT

The present invention relates to the oxidation of monoolefins with molecular oxygen to the corresponding olefin oxides, in the liquid phase in the presence of a catalyst comprising an organo-monovalent aurous complex.

2 Claims, No Drawings

ORGANO-MONOVALENT AURUS COMPLEX CATALYSTS FOR THE MANUFACTURE OF OLEFIN OXIDES

This is a division of application Ser. No. 912,620 filed June 5, 1978 now abandoned.

BACKGROUND OF THE INVENTION

The present invention relates to a novel catalytic process for the manufacture of epoxides and to the novel catalyst therefor. More particularly, the present invention relates to the manufacture of olefin oxides such as ethylene oxide, propylene oxide, butylene oxide and the like, from the corresponding olefins and molecular oxygen, in the liquid phase, in the presence of a catalyst comprising a homogeneous, organo-monovalent aurous complex.

The classic processes for the manufacture of epoxides such as propylene oxide are based on chlorohydrin or hydroperoxide technologies which involve multi-step operations. There is an increasing demand for propylene oxide and its derivatives, and consequently there exists a need for a process offering improved economics and giving both higher yields and selectivities under milder reaction conditions.

While processes are known for the direct oxidation of olefins to the corresponding epoxides with molecular oxygen using as catalysts transition metals, and especially Group VIII element complexes, these processes are characterized by low conversions, poor selectivities, short catalyst life and extreme reaction conditions. Examples of homogeneous reactions in which olefins are directly oxidized to olefin oxides include: U.S. Pat. No. 3,232,957 (1966) which relates to a non-catalytic method for the epoxidation of olefins (especially ethylene and propylene); U.S. Pat. Nos. 3,784,202 (1957), 3,071,601 (1963) and 2,985,668 (1961) which describe similar processes; D.T. No. 2,313,032 (1973) which describes the direct liquid phase oxidation of propylene in acetone solution over a silica-supported oxide of selenium, lanthanum, yttrium, indium, gallium or thallium; U.S. Pat. Nos. 3,856,826 (1974) and 3,856,827 (1974) which employ homogeneous, phosphorus-modified or silicon-containing molybdenum catalysts in a chlorobenzene solvent medium. However none of these processes report conversions or selectivities within a range acceptable for commercialization.

The process of the present invention offers the advantages of a single step process requiring only moderate temperatures and pressures. It is surprising that the monovalent gold catalysts in the present process are active for the epoxidation reaction in view of the disclosure of Fusi, et al. *J. Organometal Chemistry* 26, 417 (1971) wherein it is suggested that $d^{10}$ monovalent gold metal complexes give no sign of coordinative activity which is essential for the activation of the reactants in this type of reaction.

In accordance with the present invention, monoolefinic hydrocarbons containing from 2 to 12 carbon atoms are oxidized with molecular oxygen to the corresponding epoxides in a liquid phase reaction medium containing a soluble monovalent gold catalyst having the formula:

$$[X_m Au^{(I)} L_n][Y]_z$$

wherein

X is a uninegative coordinating anion;

L is a neutral coordinating $\pi$-acid type ligand; and

Y is a uninegative noncoordinating anion;

and wherein z = 0 or 1;

m = 0 or 1 (when z is 0, m is 1, and when m is 0, z is 1) and n = 1 to 4.

The ligand systems of the catalyst of this invention do not appear to be critical to either product level or product distribution providing they are of a labile nature. The primary role of the ligand is to compliment the electronic configuration of the metal, to stabilize the complex and to aid in the solubilization of the metal component.

In the above catalyst composition, while it is preferred that X is a halogen and L is a phosphine moiety, —PR$_3$, wherein PR$_3$ is a trialkyl, triaryl or a mixed phosphine, X may also be $OAc^-$, $SCN^-$, $S_2O_3^-$, acetyl-acetonate, $S_2CNR_2^-$, $SC_6H_5^-$, $OC(S)OR^-$, $SnCl_3^-$, $CN^-$, $Mn(CO)_5^-$, $V(CO)_6^-$, $Mn(CO)_4L^-$, $Mn(CO)_5X^-$ (wherein $X=Cl^-, Br^-, I^-$), $Os_3(CO)_{12}^-$, $Ir(CO)_3P\phi_3^-$, $M(CO)_3C_p^-$ (wherein $M = Cr$, Mo, or W), $Co(CO)_4^-$, $PtX(P\phi_3)_2^-$ (wherein $X = Cl^-, Br^-, I^-$);

L may also be $P\phi_3$, $PMe\phi_2$, $PMe_2\phi$, $PMe_3$, $PEt_3$, $P_n\text{-}Bu_3$, $As\phi_3$, $AsEt_3$, $Sb\phi_3$, $P(p\text{---}ClC_6H_4)_3$, $P(OC_6H_4CH_3)_3$, $P(C_6H_{11})_3$, $OP(OEt)_3$, $P(O_n\text{---}Bu)_3$, $NH_3$, $NR_3$, diars, diphos, $CNC_6H_5$, p—$CH_3C_6H_4NC$, P—$CH_3OC_6H_4NC$, an olefin, alkyne, or $NC_5H_5$; and Y may be $F_3CSO_3^-$, $BF_4^-$, $PR_6^-$, $ClO_4^-$, $B\phi_4^-$, $I^-$, $Cl^-$, $Br^-$, $AlCl_4^-$ or a picrate.

In the above catalyst formula, when Y is a halogen, X can not be a halogen, and n equals 2 or 4.

The catalyst of this invention may be dissolved in the reaction medium as a homogeneous catalyst, slurried in the reaction medium as an insoluble, unsupported heterogeneous catalyst, or in some cases where advantageous they may be supported on carriers such as silica, alumina or polymeric materials and slurried in the reaction medium. It is preferred however that the catalyst system be a homogeneous system where the catalyst is soluble in the reaction solvent. Catalysts insoluble in the reaction medium, however, also provide oxidation if sufficient agitation and contact time are maintained.

The concentration of the catalyst in the solvent medium may range from $10^{-6}$ to $10^{-1}$ moles per liter and more preferably the catalyst concentration may range from about $10^{-4}$ to $10^{-2}$ moles per liter.

The catalyst of this invention may be prepared by generating the monovalent gold species from gold metal and isolating prior to dissolution, or the species can be generated in situ in the following manner:

The gold (I) halide may be reacted with the appropriate ligand (L) to give X AuL$_n$ in situ. Subsequently, if desired, the addition of AgY will generate the corresponding ionic analog $[AuL_n]Y_z$. Metathetical reactions allow formation of the desired variations of X starting with either XAu or XAuL$_n$, or variations in Y starting with $[AuL_n]Y_z$. Species of the form $[AuL_n]Y$ can be generated in situ by treatment of XAu with Ag Y, where L is the reactant olefin. The yields of catalyst based on the starting amount of gold metal are generally quite high as the reactions approach stoichiometric ratios.

There is evidence to suggest that temperature conditioning of the catalyst enhances both the performance and stability of the catalyst since there appears to be an induction period required to generate the activated complex of the catalyst. This can be accomplished by gradually increasing the temperature of the catalyst solution from 50° to 200° C. over a period of time ranging from 2 to 24 hours, or more preferably, raising the temperature from 100°–150° C. over a period of at least 6 hours.

A wide variety of ethylenically unsaturated, nonbenzenoid-type hydrocarbons can be epoxidized in accordance with the invention. In general, any organic mono-olefin, preferably a hydrocarbon having from 2 to about 12 carbon atoms and more preferably mono-olefins having from 3 to 10 carbon atoms are oxidized to the corresponding epoxides. Examples of suitable aliphatic monoolefinic hydrocarbons include: ethylene, propylene, butene-1, butene-2, isobutene, pentene-1, pentene-2, hexene, isohexene, heptene, 3-methyl hexene-1, octene-1, isooctene, nonene, decene, and dodecene. Examples of suitable alicyclic olefins include: cyclopentene, cyclohexene, and cycloheptene; and cycloalkylolefins such as methyl cyclohexene, isopropyl cyclohexene, butyl cyclohexene, and the like, are contemplated to be within the scope of the invention.

The reaction medium suitable for the process of this invention is an essentially inert, non-coordinating or weakly coordinating polar organic solvent having a boiling point significantly higher than the boiling points of the feeds or the products obtained. Solvents with boiling points of from 100° to 225° C. are especially preferred. Also desirable are those solvents having an absence of abstractable hydrogens which lead to oxidation of the solvent or the binding of the active sites of the metal or metals in the catalyst, thereby deactivating the catalyst. Examples of suitable solvents include paraffinic hydrocarbons, aromatic hydrocarbons, chlorinated hydrocarbons, and nitrile aromatics, such as heptanes, decanes and the like; chloroform, carbon tetrachloride, etc.; and benzyl nitrile and the like. The most preferred solvent is benzene.

In this process it is possible to favor the formation of either the epoxide or the corresponding glycol by proper selection of the reaction conditions, since water adds readily to the epoxide to form the glycol in an acid environment. The oxidation reaction of the present invention is very sensitive to reaction conditions and it is an essential feature of the invention that the reaction be carried out under conditions which maximize selectivity to the desired product.

The reaction of this invention may be carried out at temperatures in the range of from about 50° to 250° C., and preferably at temperatures in the range of from about 75° to 150° C. Temperatures above about 200° C. however are deleterious to the catalyst life and bring about the formation of additional oxidation products such as aldehydes and increased formation of undesirable polymer.

The reaction pressure may vary with the solvent system employed. Generally pressures may range from 1 to 20 atmospheres, and preferably from 1 to 10 atmospheres. Air or oxygen may be employed in the reaction, although oxygen is preferred to air since the reaction is favored by low partial pressures of olefin and moderately high partial pressures of oxygen. Pressures in the system may be effectively increased by introducing an inert diluent such as nitrogen, carbon dioxide, helium, argon and the like.

Among the reaction variables affecting selectivity of the reaction is the ratio of olefin to oxygen. While the molar ratio of olefin to oxygen may vary from 0.01 to 100, a ratio of 0.33 to 5.0 is preferred and a ratio of 1.5 to 2 is most preferred. It is particularly important for safety reasons that the olefin to oxygen ratio fall outside the explosive limits for the olefin-oxygen mixture being reacted. With propylene, for example, this ratio falls within the range of 2.1 to 56.3% propylene in oxygen, so that mixtures containing either 2% propylene or below or 60% propylene or above are recommended.

In those instances where the reaction is carried out in a sealed reaction vessel, the reaction times may range from 0.25 to 10 hours and a reaction time of from 1.0 to 4 hours is preferable. Continuous operation in which the reaction mixture is maintained at constant temperature and pressure is contemplated to be within the scope of the present invention. Under such conditions, the olefin and air or oxygen are continuously fed to the reactor while volatile products and the unreacted feed are continuously removed. The volatile products can be collected and the unreacted feed recycled to the reactor.

The reactor vessel may be constructed from stainless steel, or in certain instances the reaction vessel may be lined with glass, quartz or a stable resinous material in order to minimize side reactions between the reaction intermediates and the walls of the reaction vessel.

SPECIFIC EXAMPLES

The present invention is illustrated by the experiments in Examples 1 to 7 in which propylene is converted to propylene oxide. These data are summarized in Table I.

The percent conversion of propylene and the percent yield of propylene oxide reported are based on the percent of propylene reacted.

EXAMPLES 1 TO 7

The oxidation of propylene to propylene oxide in the presence of a variety of gold catalyst complexes was conducted in a series of experiments according to the following procedure:

An amount of catalyst required to give a concentration of $1 \times 10^{-4}$ moles of catalyst in the reaction solvent was weighed into a stainless steel reaction tube (180 millimeters long $\times$ 9.5 millimeter diameter) equipped with a stainless steel ball valve and septum cap. The tube was evacuated and charged with a mixture of propylene and oxygen at an initial pressure of 20 atmospheres. Four milliliters of solvent were introduced into the tube with a metering pump. The tube and its contents were heated to a temperature of 150° C. in a heating block for a period of two hours. At the end of this time the tube was quickly cooled to room temperature and the reaction mixture analyzed by gas chromotography.

TABLE I

| Example No. | Catalyst | Solvent | Reaction Conditions $C_3=/O_2$ (Molar) | Rx. Temp. °C. | Rx. Time Hrs. | % Conversion | Percent Yield Propylene Oxide | Propylene Glycol |
|---|---|---|---|---|---|---|---|---|
| 1 | [Au(PEt$_3$)]F$_3$CSO$_3$[A] | CH$_2$Cl$_2$ | 2/98 | 125 | 8 | 50 | 20 | |
| 2 | [Au(As$\phi_3$)]F$_3$CSO$_3$[B] | Benzene | 2/98 | 150 | 2 | 80 | 20 | |

TABLE I-continued

| Example No. | Catalyst | Solvent | Reaction Conditions | | | % Conversion | Percent Yield | |
|---|---|---|---|---|---|---|---|---|
| | | | $C_3^=/O_2$ (Molar) | Rx. Temp. °C. | Rx. Time Hrs. | | Propylene Oxide | Propylene Glycol |
| 3 | Au(Pϕ$_3$)I[A] | CH$_2$Cl$_2$ | 2/98 | 125 | 8 | 30 | 5 | 20 |
| 4 | Au(AsEt$_3$)(AlCl$_4$) | CH$_2$Cl$_2$ | 2/98 | 150 | 2 | 75 | 25 | 25 |
| 5 | (Pϕ$_3$)Au—Mn(CO)$_5$ | CH$_2$Cl$_2$ | 2/98 | 150 | 2 | 50 | 15 | |
| 6 | ClAuPEt$_3$ | ClC$_6$H$_5$ | 2/98 | 60 | 2 | 25 | 10 | |
| 7 | ClAuPϕ$_3$ | ClC$_6$H$_5$ | 2/98 | 60 | 2 | 15 | 4.5 | |

[A]Catalyst activated in situ 2 hrs. @ 100° C.
[B]Catalyst activated in situ 2 hrs. both at 100 and 125° C.

We claim:

1. The catalyst complex represented by the empirical formula:

$$Au^I LY$$

wherein

L is a neutral coordinating π-acid type ligand; and
Y is a uninegative non-coordinating anion selected from the group consisting of $F_3CSO_3^-$, $BF_4^-$, $PF_6^-$, $ClO_4^-$, $AlCl_4^-$ and picrate.

2. The catalyst complex of claim 1 wherein Y is $F_3CSO_3^-$ or $AlCl_4^-$.

* * * * *